United States Patent
Airaksinen et al.

(10) Patent No.: US 10,492,733 B2
(45) Date of Patent: Dec. 3, 2019

(54) METHOD AND APPARATUS FOR DETERMINING INFORMATION INDICATIVE OF CARDIAC MALFUNCTIONS AND ABNORMALITIES

(71) Applicant: TURUN YLIOPISTO, Turun Yliopisto (FI)

(72) Inventors: Juhani Airaksinen, Turku (FI); Tero Koivisto, Turku (FI); Joona Marku, Turku (FI); Ari Paasio, Littoinen (FI); Mikko Pankaala, Raisio (FI); Kati Sairanen, Naantali (FI); Tuomas Valtonen, Turku (FI); Peter Virta, Turku (FI)

(73) Assignee: PRECORDIOR OY, Turku (FI)

( * ) Notice: Subject to any disclaimer, the term of this patent is extended or adjusted under 35 U.S.C. 154(b) by 1302 days.

(21) Appl. No.: 14/396,214

(22) PCT Filed: Apr. 17, 2013

(86) PCT No.: PCT/FI2013/050422
§ 371 (c)(1),
(2) Date: Oct. 22, 2014

(87) PCT Pub. No.: WO2013/160538
PCT Pub. Date: Oct. 31, 2013

(65) Prior Publication Data
US 2015/0065894 A1 Mar. 5, 2015

(30) Foreign Application Priority Data

Apr. 23, 2012 (FI) .................................. 20125441

(51) Int. Cl.
*A61B 5/02* (2006.01)
*A61B 5/00* (2006.01)
(Continued)

(52) U.S. Cl.
CPC .......... *A61B 5/7282* (2013.01); *A61B 5/0002* (2013.01); *A61B 5/0205* (2013.01);
(Continued)

(58) Field of Classification Search
CPC ....... A61B 5/1102; A61B 5/00; A61B 5/0205; A61B 5/725; A61B 5/11; A61B 5/7282;
(Continued)

(56) References Cited

U.S. PATENT DOCUMENTS

2003/0233034 A1* 12/2003 Varri .................... A61B 5/1102
600/301
2006/0095085 A1* 5/2006 Marcus ................ A61B 5/1107
607/17
(Continued)

FOREIGN PATENT DOCUMENTS

| WO | 92/20284 A1 | 11/1992 |
| WO | 2005/011475 A2 | 2/2005 |
| WO | 2012/149652 A1 | 5/2012 |

OTHER PUBLICATIONS

Inan O T et al.: "Robust ballistocardiogram acquisition for home monitoring", Physiological Measurement, Institute of Physics Publishing, Bristol, GB, vol. 30, No. 2, Feb. 1, 2009 (Feb. 1, 2009), pp. 169-185, XP020153654, ISSN: 0967-3334, 001: 10.1088/0967-3334/30/2/005 p. 172, line 1—p. 173, line 22 p. 179, line 1—p. 181, line 21 table 1 figures 4,5.
(Continued)

*Primary Examiner* — Eric J Messersmith
(74) *Attorney, Agent, or Firm* — Young & Thompson

(57) ABSTRACT

An apparatus for determining information indicative of cardiac malfunctions and abnormalities includes a processing device (502) configured to detect amplitude variation from a signal indicative of cardiovascular motion, where the amplitude variation element variation of the amplitude of a
(Continued)

wave pattern, e.g. the AO-peak, repeating on the heart-beat rate on the signal. The processing device is configured to determine, at least partly on the basis of the detected amplitude variation, an indicator of cardiac malfunction and abnormality.

16 Claims, 8 Drawing Sheets

(51) Int. Cl.
*A61B 5/0205* (2006.01)
*A61B 5/08* (2006.01)
*A61B 5/11* (2006.01)
*A61B 5/024* (2006.01)
*G01B 21/22* (2006.01)
*G01L 1/00* (2006.01)
*G01P 15/00* (2006.01)
*G01R 29/22* (2006.01)
*G16H 50/30* (2018.01)
*G01R 19/04* (2006.01)

(52) U.S. Cl.
CPC ...... *A61B 5/02405* (2013.01); *A61B 5/02438* (2013.01); *A61B 5/0816* (2013.01); *A61B 5/1102* (2013.01); *A61B 5/1126* (2013.01); *A61B 5/725* (2013.01); *G01B 21/22* (2013.01); *G01L 1/00* (2013.01); *G01P 15/00* (2013.01); *G01R 29/22* (2013.01); *G16H 50/30* (2018.01); *G01R 19/04* (2013.01)

(58) Field of Classification Search
CPC .. A61B 5/02405; A61B 5/0002; G01B 21/22; G01L 1/00; G01P 15/00; G06F 19/3431; G06F 19/00; G01R 29/22
See application file for complete search history.

(56) References Cited

U.S. PATENT DOCUMENTS

| 2006/0293605 | A1 | 12/2006 | Zanetti et al. |
| 2008/0194975 | A1 | 8/2008 | Macquarrie et al. |
| 2009/0163815 | A1 | 6/2009 | Kawagishi et al. |
| 2010/0210921 | A1 | 8/2010 | Park et al. |
| 2011/0066042 | A1 | 3/2011 | Pandia et al. |
| 2011/0118614 | A1* | 5/2011 | Brauers .............. A61B 5/02438 600/500 |
| 2011/0130671 | A1 | 6/2011 | Macquarrie et al. |
| 2011/0263994 | A1* | 10/2011 | Burns .................. A61B 5/0006 600/509 |
| 2012/0123279 | A1* | 5/2012 | Brueser ................ A61B 5/1102 600/481 |

OTHER PUBLICATIONS

Dinh A., et al., A heart rate sensor based on seismocardiography for vital sign monitoring systems, 24th Canadian Conference on Electrical and Computer Engineering, Aug. 5, 2011, Conference Proceeding Article, pp. 665-668 <doi: 10.1109/CCECE.2011.6030536> the whole document.

International Search Report, dated Jul. 22, 2013, from corresponding PCT application.

FI Search Report, dated Dec. 21, 2012, from corresponding FI application.

* cited by examiner

METHOD AND APPARATUS FOR DETERMINING INFORMATION INDICATIVE OF CARDIAC MALFUNCTIONS AND ABNORMALITIES

FIELD OF THE INVENTION

The invention relates generally to determining information indicative of cardiac malfunctions and abnormalities, such as for example atrial fibrillation. More particularly, the invention relates to an apparatus and to a method for determining information indicative of cardiac malfunctions and abnormalities. Furthermore, the invention relates to a computer program for determining information indicative of cardiac malfunctions and abnormalities.

BACKGROUND

Malfunctions and abnormalities that may occur in the cardiovascular system, if not diagnosed and appropriately treated or remedied, may progressively decrease the ability of the cardiovascular system to supply, inter alia, sufficient oxygen to satisfy the coronary oxygen demand when the individual encounters stress. Currently, methods such as cardiography based on electromagnetic phenomena related to cardiac activity, echocardiography, and cardiography based on cardiovascular motion are used in the identification and assessment of various cardiac malfunctions and abnormalities. A well-known example of the cardiography based on electromagnetic phenomena related to cardiac activity is the electrocardiography "ECG", and examples of the cardiography based on cardiovascular motion are ballistocardiography "BCG" and seismocardiography "SCG". The echocardiography provides images of sections of the heart and can provide comprehensive information about the structure and function of the heart, but requires expensive equipment and specialised operating personnel. The ECG provides a fairly rapid electrical assessment of the heart but an inconveniency related to the ECG is the need to attach electrodes to the skin of the individual, which may result in skin irritation especially in long lasting and/or frequently repeating use. On the other hand, certain cardiac malfunctions and abnormalities such as, for example, atrial fibrillation may require long lasting and/or repetitive measuring of cardiograph data. The cardiography based on cardiovascular motion involves measurement of a signal indicative of cardiovascular motion. Earlier, the signal was obtained while an individual lay on a bed that was provided with an apparatus for measuring movements or there was a facilitating apparatus that was attached across the shin area of the legs. Currently, the signal can be obtained using small sensor elements, e.g. accelerometers, which are suitable for measuring minute movements which are representative of movements of the heart.

FIGS. 1a and 1b show the relationship between rhythmic electrical functions and related cardiovascular motions. FIG. 1a shows an example of an ECG waveform and FIG. 1b shows a waveform of an exemplifying signal indicative of cardiovascular motion and measured with an accelerometer in the "head-to-foot"-direction that is typically referred to as the y-direction. For the sake of illustrative purposes, a brief explanation of basic heart functions is provided below.

The heart includes four chambers. The right atrium is interconnected with the right ventricle by the tricuspid valve, and the left atrium is interconnected with the left ventricle by the mitral valve. Blood is delivered to the right atrium from the upper half of the body via the superior vena cava, and from the lower half of the body via the inferior vena cava. The tricuspid valve is opened by concurrent contraction of the right atrium myocardium and the right ventricular papillary muscles thereby allowing blood flow from the right atrium into the right ventricle. Then the tricuspid valve closes when the papillary muscles relax. When the myocardium of the right ventricle contracts, blood is forced from the right ventricle through the pulmonary valve into the pulmonary artery which delivers the blood into the lungs wherein it is oxygenated. The oxygenated blood is then delivered to the left atrium via pulmonary veins. The oxygenated blood flows from the left atrium into the left ventricle when the mitral valve is opened by concurrent contraction of the left atrium myocardium and the left ventricular papillary muscles thereby allowing blood flow from the left atrium into the left ventricle. Then the mitral valve is closed when the papillary muscles relax. The oxygenated blood is then forced out from the left ventricle through the aortic valve into the aorta which delivers the oxygenated blood to the peripheral vascular system.

Each heart-beat period involves three major stages: the atrial systole, the ventricular systole and the cardiac diastole. The atrial systole is the period of contraction of the heart muscles encompassing the right and left atria. Both atria contract concurrently with the papillary muscle contraction thereby forcing open the tricuspid valve and the mitral valve. The electrical activity, i.e. the electrical systole, which stimulates the muscle tissue of the chambers of the heart to make them contract begins in the sinoatrial node located in the right atrium. The conduction electrical depolarization continues to travel as a wave downwards, leftwards, and posteriorly through both atria depolarising each atrial muscle cell in turn. This propagation of charge can be seen as the P-wave on the ECG waveform shown in FIG. 1a. This is closely followed by mechanical contraction of the atria that is detected as an impact which corresponds to the h-peak of the waveform shown in FIG. 1b and to a recoil which corresponds to the i-valley of the waveform shown in FIG. 1b. When the right and left atria begin to contract, there is a high velocity flow of blood into the right and left ventricles, which is represented by the j-peak on the waveform shown in FIG. 1b. The continuing atrial contraction, when the tricuspid valve begins to close, causes an additional lower velocity flow of blood into the right and left ventricles. The additional flow of blood is called the "atrial kick", which corresponds to the "a-a$^1$"-wave complex in the waveform shown in FIG. 1b. After the atria are emptied, the tricuspid and mitral valves close thereby giving rise to the downward g-wave on the waveform shown in FIG. 1b. The ventricular systole is the contraction of the muscles of the left and right ventricles, and is caused by the electrical depolarization of the ventricular myocardia giving rise to the "Q-R-S"-wave complex in the ECG waveform shown in FIG. 1a. The downward Q-wave is caused by the downward flow of depolarisation through the septum along a specialized group of cells called "the bundle of His". The R-peak is caused by depolarization of the ventricular muscle tissue, and the S-wave is produced by depolarization of the heart tissue between the atria and ventricles. As the depolarization travels down the septum and throughout the ventricular myocardia, the atria and sinoatrial node start to polarise. The closing of the tricuspid and mitral valves mark the beginning of ventricular systole and cause the first part of the "lub-dub" sound made by the heart as it beats. This sound is typically known as the "first heart tone". When the electrical depolarization of the ventricular myocardia peaks, the atrioventricular "AV" septum separating the right and left ventricles contracts causing an impact, which corresponds to the H-peak on the waveform shown in FIG. 1b, and a recoil which corresponds to the I-valley on the waveform shown in FIG. 1b. The ventricular contraction forces the blood from the right ventricle into the pulmonary artery through the pulmonary valve, and from the left ventricle into the aorta through the aortic valve under very high velocity thereby causing the J-peak on the waveform shown in FIG. 1b. The deceleration of blood flow from the left ventricle into the aorta causes the downward K-wave on the waveform shown in FIG. 1b. When the left ventricle empties, its pressure falls below the pressure in the aorta and the aortic valve closes. Similarly, when the pressure in the right ventricle falls below the pressure in the pulmonary artery, the pulmonary valve closes. The second part of the "lub-dub" sound, which is typically known as the "second heart tone", is caused by the closure of the pulmonary and aortic valves at the end of ventricular systole thereby causing the upward L-wave on the waveform shown in FIG. 1b. Concurrently with the closing of the pulmonary and aortic valves, the atrioventricular "AV" septum relaxes and moves upward, and the ventricular myocardia is re-polarized giving rise to the T-wave on the ECG waveform shown in FIG. 1a. The cardiac diastole, which includes the atrial diastole and the ventricular diastole, is the period when the heart relaxes after contraction and prepares for being refilled with circulating blood. Atrial diastole is when the right and left atria are relaxing, and the ventricular diastole is when the right and left ventricles are relaxing. During the period of the atrial diastole, the right atrium is re-filled by deoxygenated blood while the left atrium is re-filled with oxygenated blood. Re-filling of the atria causes the downward M-wave on the waveform shown in FIG. 1b early in the diastole which coincides with repolarization of the bundle of His cells, which is shown as the U-wave in the ECG waveform. When the right and left atria are filled to their maximum capacities, the reflux of blood against the tricuspid valve and mitral valve cause the upward N-wave on the waveform shown in FIG. 1b.

Publication WO2012149652 describes a method for assessment of cardiac contractility in a subject by recording precordial acceleration signals.

Publication US2008194975 describes a method for monitoring an individual's physiological condition and detecting abnormalities therein. The method comprises concurrently receiving a first signal that is an ECG signal and a second signal indicative of cardiovascular motion.

Analysis of waveforms indicative of cardiovascular motion is typically performed visually by qualified diagnosticians in order to distinguish abnormal cardiovascular function from normal cases. In many cases, however, it may be challenging to find out certain cardiac malfunctions and abnormalities, such as for example atrial fibrillation, by visual analysis. Thus, a need exists for methods and apparatuses for determining information indicative of cardiac malfunctions and abnormalities.

SUMMARY

In accordance with the invention, there is provided a new method for determining information indicative of cardiac malfunctions and abnormalities, e.g. atrial fibrillation. The method according to the invention comprises:

detecting peak-to-peak amplitude variation from a signal indicative of cardiovascular motion, the peak-to-peak amplitude variation being variation of peak-to-peak amplitude of a wave pattern repeating on the heart-beat rate on the signal so that the peak-to-peak amplitude variation includes a plurality of increases of the peak-to-peak amplitude and a plurality of decreases of the peak-to-peak amplitude, computing a signal component of the peak-to-peak amplitude variation having a frequency of a respiratory rhythm, and producing a signal expressing atrial fibrillation in response to a situation in which the signal component of the peak-to-peak amplitude variation having the frequency of the respiratory rhythm is less than a threshold.

The above-mentioned wave pattern can be, for example but not necessarily, the J-peak on the waveform shown in FIG. 1b, and the amplitude of the wave pattern can be the signal value of the top of the J-peak. For another example, the wave pattern can be the wave complex constituted by the J-peak and the downward K-wave on the waveform shown in FIG. 1b, and the amplitude of the wave pattern can be the peak-to-peak value from the bottom of the downward K-wave to the top of the J-peak. For one example, the wave pattern can be the AO-peak caused by openings of the aortic valve on a waveform measured in the "through chest"-direction that is typically referred to as the z-direction. For one example, the wave pattern can be the wave complex constituted by the AO-peak and the downward wave that follows the AO-peak.

Such cardiac malfunctions and abnormalities, e.g. atrial fibrillation, which may be sometimes challenging to diagnose, may however cause irregularities on the waveform of the signal indicative of cardiovascular motion. These irregularities may be difficult to detect from waveforms of one or two heart-beat periods but they may manifest themselves in longer time periods covering several heart-beat periods so that the amplitude of the wave pattern repeating on the heart-beat rate varies more strongly than in a normal case. Therefore, the amplitude variation represents information indicative of cardiac malfunction and abnormality.

A method according to an exemplifying embodiment of the invention further comprises detecting time variation from the signal, where the time variation is the variation of temporal lengths of heart-beat periods. The indicator of cardiac malfunction and abnormality can be determined on the basis of both the amplitude variation and the time variation in order to improve the reliability of the information indicative of cardiac malfunctions and abnormalities.

A method according to an exemplifying embodiment of the invention comprises low-pass filtering a signal indicative of cardiovascular motion and detecting AO-peaks from the low-pass filtered signal and/or band-pass filtering the signal indicative of the cardiovascular motion and detecting AC-peaks from the band-pass filtered signal, where the AO-peaks are caused by the openings of the aortic valve and the AC-peaks are caused by the closures of the aortic valve. The upper limit frequency of the low-pass filtering can be, for example but not necessarily, 30 Hz, and the pass-band of the band-pass filtering can be, for example but not necessarily, from 40 Hz to 100 Hz. The low-pass filtering and/or the pass-band filtering facilitate the detection of the AO- and/or AC-peaks. Especially during atrial fibrillation, the AC-peaks are easier to find when the band-pass filtering is used than when there is no band-pass filtering. The detected AO- and/or AC-peaks can be utilized when detecting for example the above-mentioned amplitude variation, the above-mentioned time variation, the heart-beat rate, the systolic intervals, and/or the diastolic intervals.

In accordance with the invention, there is provided also a new apparatus for determining information indicative of cardiac malfunctions and abnormalities. The apparatus according to the invention comprises:
  a signal interface for receiving a signal indicative of cardiovascular motion and for receiving information indicative of a frequency of a respiratory rhythm, and
  a processing device coupled to the signal interface and configured to:
  a) detect peak-to-peak amplitude variation from the signal, the peak-to-peak amplitude variation being variation of peak-to-peak amplitude of a wave pattern repeating on the heart-beat rate on the signal so that the peak-to-peak amplitude variation includes a plurality of increases of the peak-to-peak amplitude and a plurality of decreases of the peak-to-peak amplitude,
  compute a signal component of the peak-to-peak amplitude variation having the frequency of the respiratory rhythm, and
  c) produce a signal expressing atrial fibrillation in response to a situation in which the signal component of the peak-to-peak amplitude variation having the frequency of the respiratory rhythm is less than a threshold.

The apparatus may further comprise a sensor element for measuring the signal indicative of cardiovascular motion. The sensor element may comprise, for example, an accelerometer, a piezo-electronic sensor, an inclinometer, a pressure sensor, or any other element suitable for measuring force, acceleration, displacement, or any other quantity related to and indicative of cardiovascular motion. It is also possible that the signal interface is capable of receiving the signal from an external device comprising a sensor element, i.e. it is emphasized that the apparatus does not necessarily comprise any sensor element for measuring the signal indicative of cardiovascular motion.

An advantage of using the signal indicative of cardiovascular motion with respect to the ECG is that there is no need to provide electrical contact to the individual's skin and thus the skin irritation can be significantly minor especially in long lasting and/or repetitive use. Furthermore, the sensor element can be integrated to clothes and it can be provided with a radio transmitter which transmits the measured signal over a radio link. This facilitates long lasting and repetitive measurements.

An apparatus according to an exemplifying embodiment of the invention comprises a low-pass filter for low-pass filtering a signal indicative of the cardiovascular motion and means, e.g. a processor, for detecting the AO-peaks from the low-pass filtered signal and/or a band-pass filter for band-pass filtering the signal indicative of the cardiovascular motion and means for detecting the AC-peaks from the band-pass filtered signal.

In accordance with the invention, there is provided also a new computer program for determining information indicative of cardiac malfunctions and abnormalities. The computer program comprises computer executable instructions for controlling a programmable processor to:
  detect peak-to-peak amplitude variation from a signal indicative of cardiovascular motion, the peak-to-peak amplitude variation being variation of peak-to-peak amplitude of a wave pattern repeating on the heart-beat rate on the signal,
  compute a signal component of the peak-to-peak amplitude variation having a frequency of a respiratory rhythm, and
  produce a signal expressing atrial fibrillation in response to a situation in which the signal component of the peak-to-peak amplitude variation having the frequency of the respiratory rhythm is less than a threshold.

A computer program according to an exemplifying embodiment of the invention comprises computer executable instructions for controlling a programmable processor to low-pass filter a signal indicative of the cardiovascular motion and to detect the AO-peaks from the low-pass filtered signal and/or computer executable instructions for controlling the programmable processor to band-pass filter the signal indicative of the cardiovascular motion and to detect the AC-peaks from the band-pass filtered signal.

In accordance with the invention, there is provided also a new computer program product. The computer program product comprises a non-volatile computer readable medium, e.g. a compact disc "CD", encoded with a computer program according to the invention.

A number of exemplifying embodiments of the invention are described in accompanied dependent claims.

Various exemplifying embodiments of the invention both as to constructions and to methods of operation, together with additional objects and advantages thereof, will be best understood from the following description of specific exemplifying embodiments when read in connection with the accompanying drawings.

The verbs "to comprise" and "to include" are used in this document as open limitations that neither exclude nor require the existence of also un-recited features. The features recited in depending claims are mutually freely combinable unless otherwise explicitly stated.

BRIEF DESCRIPTION OF THE FIGURES

The exemplifying embodiments of the invention and their advantages are explained in greater detail below with reference to the accompanying drawings, in which:

FIGS. 1a and 1b have already been explained when describing the background of the invention.

DESCRIPTION OF THE EXEMPLIFYING EMBODIMENTS

Figure 2A:
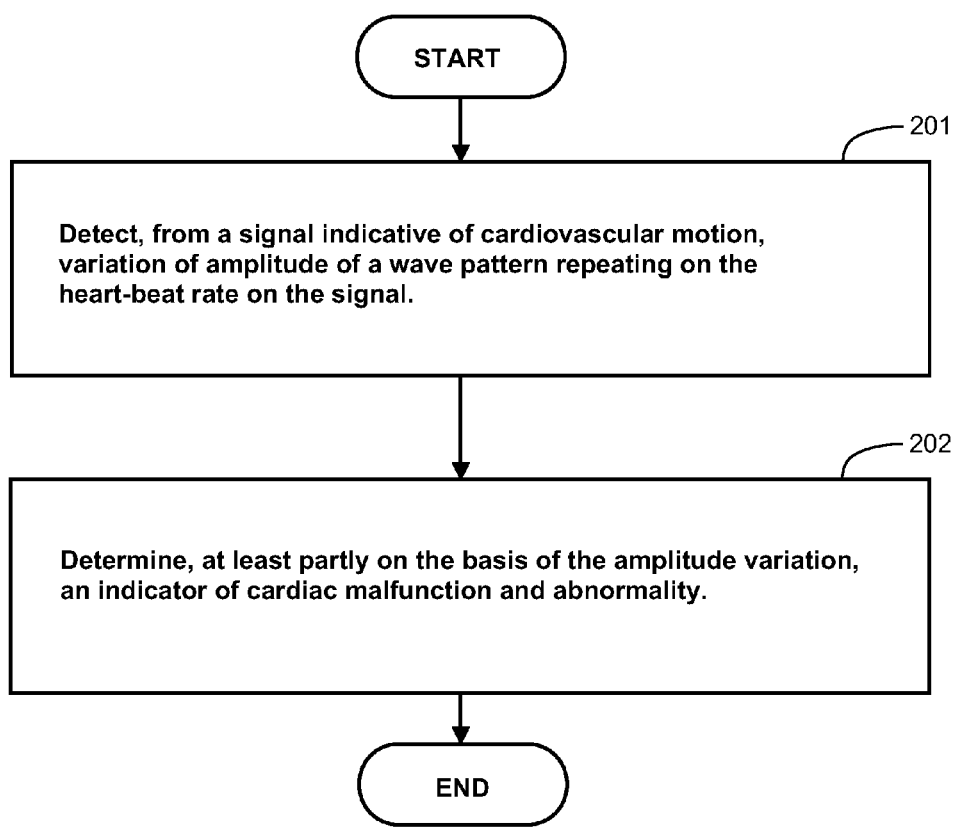
FIG. 2a illustrates a flow chart of a method according to an exemplifying embodiment of the invention for determining information indicative of cardiac malfunctions and abnormalities.

FIG. 2a illustrates a flow chart of a method according to an exemplifying embodiment of the invention for determining information indicative of cardiac malfunctions and abnormalities, e.g. atrial fibrillation. The method comprises in a phase 201 detecting amplitude variation from a signal indicative of cardiovascular motion, where the amplitude variation means variation of amplitude of a wave pattern repeating on the heart-beat rate on the signal. The method comprises in a phase 202 determining, at least partly on the basis of the detected amplitude variation, an indicator of cardiac malfunction and abnormality.

Figure 3A:
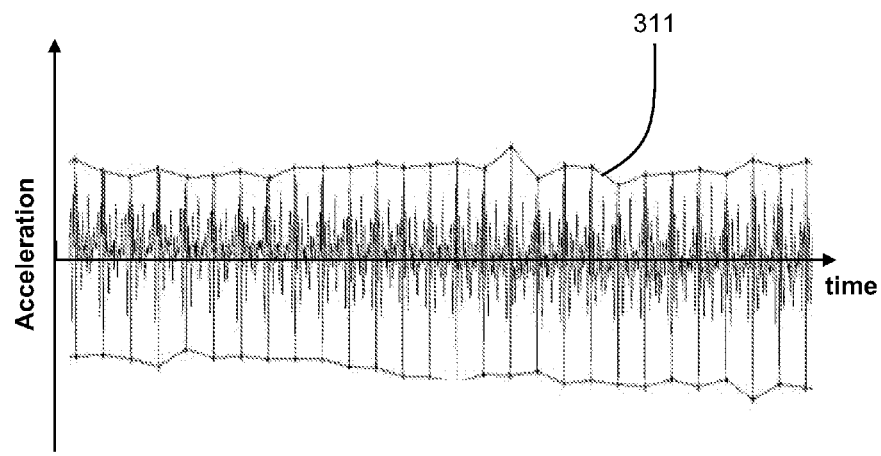
FIG. 3a illustrates a waveform of an exemplifying signal indicative of cardiovascular motion over several heart-beat periods in a normal case when a person under consideration holds breath.
Figure 3B:
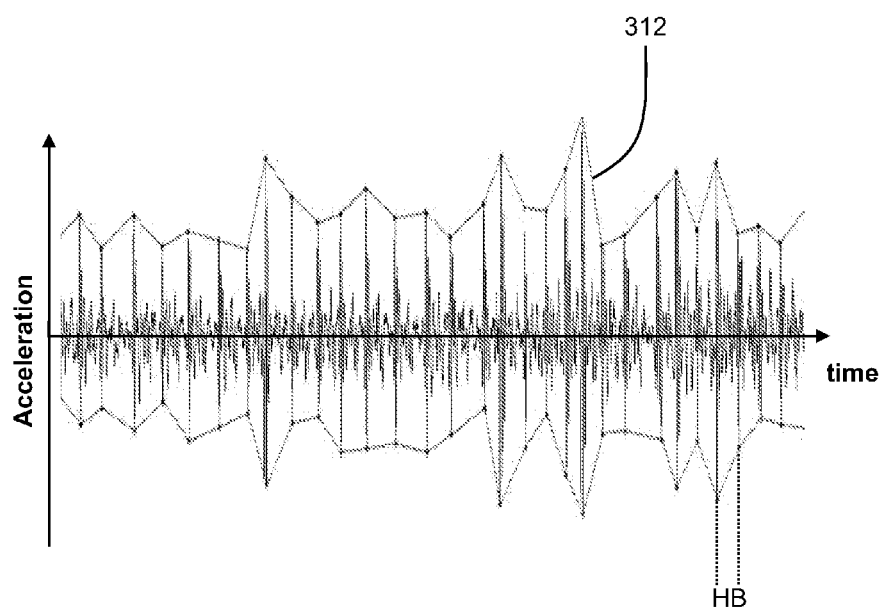
FIG. 3b illustrates a waveform of an exemplifying signal indicative of cardiovascular motion over several heart-beat periods in a case of atrial fibrillation when a person under consideration holds breath, these waveforms have been measured with an accelerometer in the "through chest"-direction that is typically referred to as the z-direction.
Figure 5:
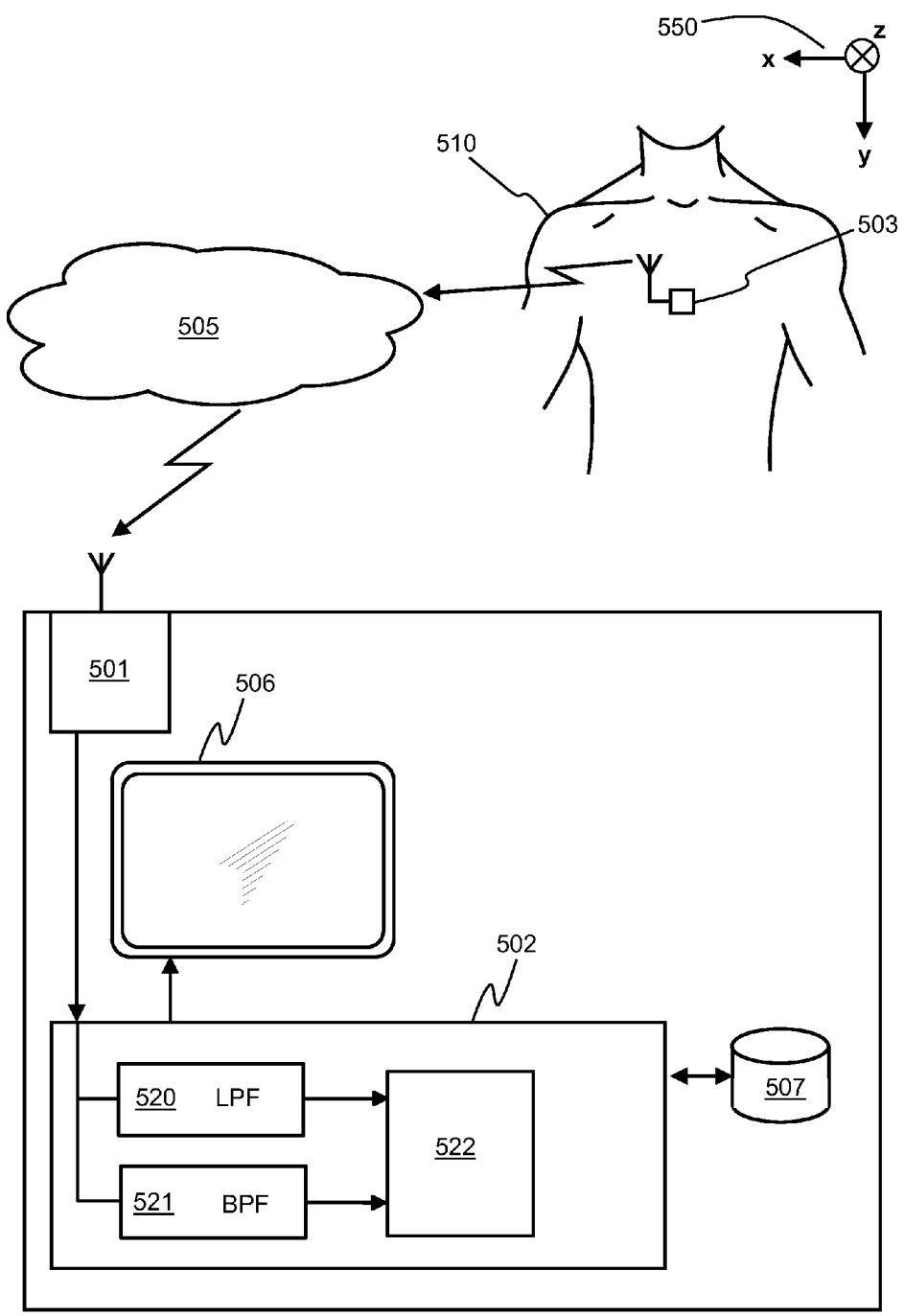
FIG. 5 shows a schematic illustration of an apparatus according to an exemplifying embodiment of the invention for determining information indicative of cardiac malfunctions and abnormalities.

FIG. 3a illustrates an exemplifying waveform of the above-mentioned signal over several heart-beat periods in an exemplifying normal case when a person under consideration holds breath, and FIG. 3b illustrates an exemplifying waveform of the signal over several heart-beat periods in an exemplifying case of atrial fibrillation when a person under consideration holds breath. The waveforms shown in FIGS. 3a and 3b have been measured with an accelerometer in the "through chest"-direction that is typically referred to as the z-direction. A coordinate system 550 shown in FIG. 5 illustrates the z-direction.

Figure 3C:
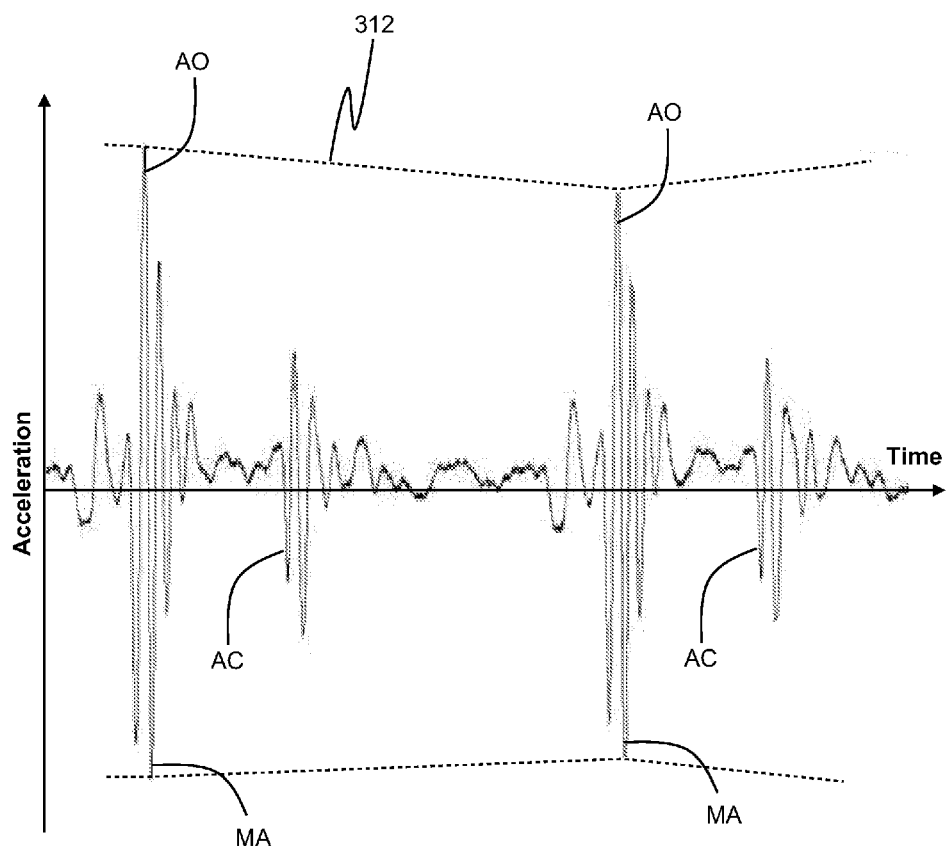
FIG. 3c shows a part of the waveform shown in FIG. 3b.

The amplitude variation in the normal case is illustrated by an envelope curve 311 shown in FIG. 3a, and the amplitude variation in the exemplifying case of atrial fibrillation is illustrated with an envelope curve 312 shown in FIGS. 3b and 3c. As can be seen from FIG. 3b, the amplitude variation includes a plurality of increases of the amplitude and a plurality of decreases of the amplitude within about ten successive heart-beat periods HB, and the increases and the decreases are interleaved with each other in a substantially stochastic way. As illustrated by FIGS. 3a and 3b, the strength of the amplitude variation represents information indicative of cardiac malfunction and abnormality.

Figure 3D:
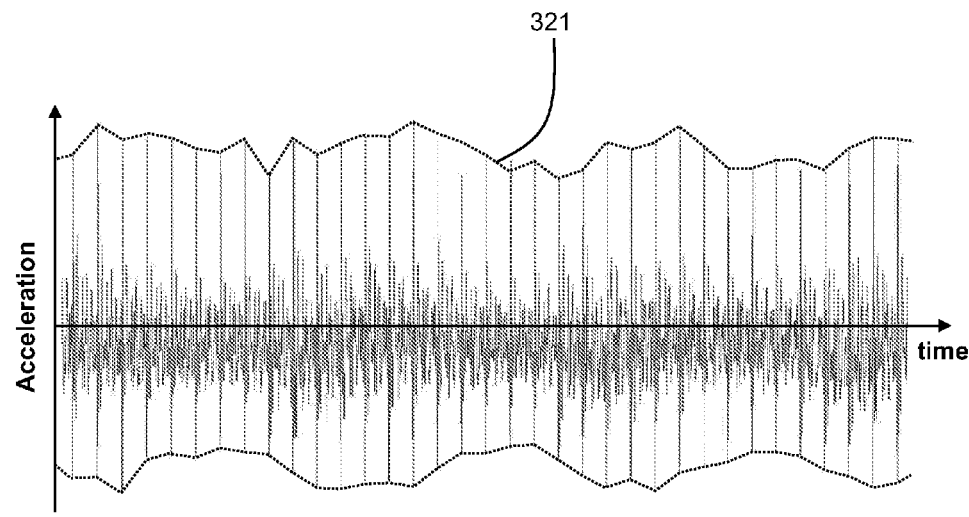
FIG. 3d illustrates a waveform of an exemplifying signal indicative of cardiovascular motion over several heart-beat periods in a normal case when a person under consideration is breathing.
Figure 3E:
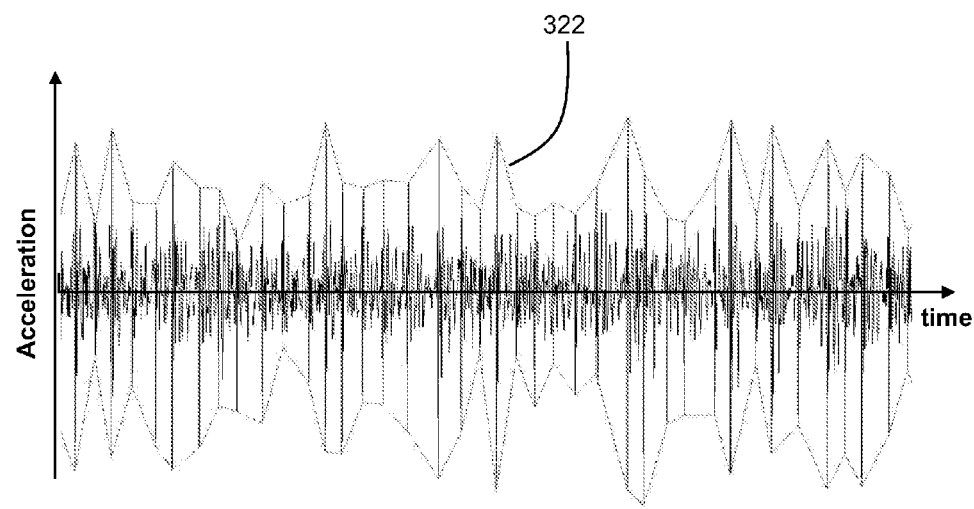
FIG. 3e illustrates a waveform of an exemplifying signal indicative of cardiovascular motion over several heart-beat periods in a case of atrial fibrillation when a person under consideration is breathing, these waveforms have been measured with an accelerometer in the "through chest"-direction that is typically referred to as the z-direction.

FIG. 3d illustrates an exemplifying waveform of the above-mentioned signal over several heart-beat periods in an exemplifying normal case when a person under consideration is breathing, and FIG. 3e illustrates an exemplifying waveform of the signal over several heart-beat periods in an exemplifying case of atrial fibrillation when a person under consideration is breathing. The waveforms shown in FIGS. 3d and 3e have been measured with an accelerometer in the "through chest"-direction that is typically referred to as the z-direction. A coordinate system 550 shown in FIG. 5 illustrates the z-direction. The amplitude variation in the normal case is illustrated by an envelope curve 321 shown in FIG. 3d, and the amplitude variation in the exemplifying case of atrial fibrillation is illustrated with an envelope curve 322 shown in FIG. 3e. As can be seen from FIG. 3d, the amplitude variation in the normal case has a clear signal component having the frequency of the breathing rhythm.

As can be seen from FIG. 3e, there is no clear signal component having the frequency of the breathing rhythm in the case of atrial fibrillation.

In a method according to an exemplifying embodiment of the invention:
the detection of the amplitude variation, i.e. the phase 201 shown in FIG. 2a, comprises computing the above-mentioned signal component of the amplitude variation having the frequency of the respiratory rhythm, and
the determining of the indicator of cardiac malfunction and abnormality, i.e. the phase 202, comprises determining the indicator of cardiac malfunction and abnormality at least partly on the basis of the strength of the signal component of the amplitude variation having the frequency of the respiratory rhythm.

The signal component of the amplitude variation having the frequency of the respiratory rhythm can be computed, for example, in the same way as a Fourier component having a given frequency is computed, i.e. by correlating a time trend of the amplitude with sine and/or cosine functions having the frequency of the respiratory rhythm.

The above-mentioned signal component of the amplitude variation having the frequency of the respiratory rhythm is indicative of cardiac malfunction and abnormality, and it can be compared to a threshold in order to detect occurrence of cardiac malfunction and abnormality. The threshold can be determined on the basis of empirical data gathered from a group of patients and/or other persons. The threshold is not necessary a constant but the threshold can be changing according to the individual under consideration, according to time, and/or according to some other factors. It is also possible to construct a series of thresholds so that each threshold represents a specific probability of atrial fibrillation or some other cardiac malfunction and/or abnormality.

FIG. 3c shows a part of the waveform shown in FIG. 3b. The waveform comprises AO-peaks caused by openings of the aortic valve and downwards waves MA each of which takes place just after the respective AO-peak.

In a method according to an exemplifying embodiment of the invention:
the detection of the amplitude variation, i.e. the phase 201 shown in FIG. 2a, comprises detecting peak-to-peak values related to wave complexes each of which being constituted by the AO-peak and the downward wave MA following the AO-peak, and
the determining of the indicator of cardiac malfunction and abnormality, i.e. the phase 202, comprises computing an amplitude variation quantity indicative of the strength of the variation of the detected peak-to-peak values.

The amplitude variation quantity is indicative of cardiac malfunction and abnormality and it can be compared to a threshold in order to detect occurrence of cardiac malfunction and abnormality. The threshold can be determined on the basis of empirical data gathered from a group of patients and/or other persons. The threshold is not necessary a constant but the threshold can be changing according to the individual under consideration, according to time, and/or according to some other factors. It is also possible to construct a series of thresholds so that each threshold represents a specific probability of atrial fibrillation or some other cardiac malfunction and/or abnormality.

The amplitude variation quantity can be, for example:

$$RMS_{p\text{-}p} - AVE_{p\text{-}p},$$

where $RMS_{p\text{-}p}$ is the root-mean-square "RMS" of the detected peak-to-peak values and $AVE_{p\text{-}p}$ is the arithmetic average of the detected peak-to-peak values. For another example, the strength of the amplitude variation can be expressed with the aid of the standard deviation of the detected peak-to-peak values, i.e. amplitude variation quantity can be the standard deviation of the detected peak-to-peak values.

Furthermore, the amplitude variation quantity can be indicative of variation of a ratio S1/S2 or of a difference S1−S2, where:
- S1 is a signal indicative of cardiovascular motion measured in the "through chest"-direction, i.e. the z-direction, and
- S2 is a signal indicative of cardiovascular motion measured in the "head-to-foot"-direction, i.e. the y-direction.

The coordinate system 550 shown in FIG. 5 illustrates the y- and z-directions.

Figure 1A:
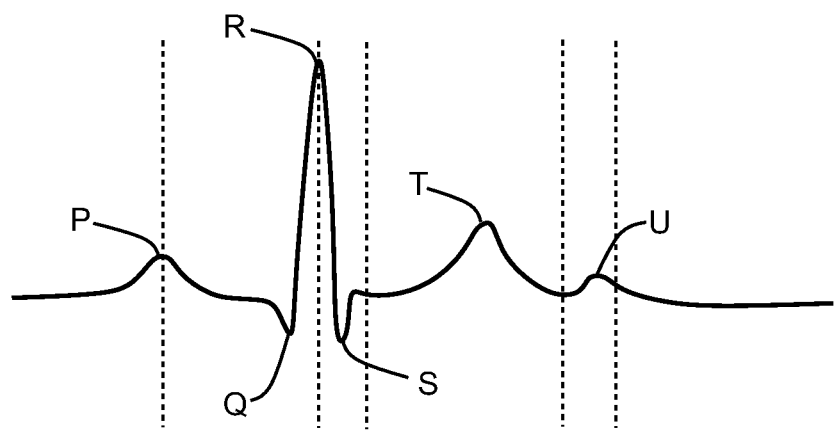
FIG. 1a illustrates an example of an ECG waveform and FIG. 1b illustrates a waveform of an exemplifying signal indicative of cardiovascular motion and measured with an accelerometer in the "head-to-foot"-direction that is typically referred to as the y-direction.
Figure 1B:
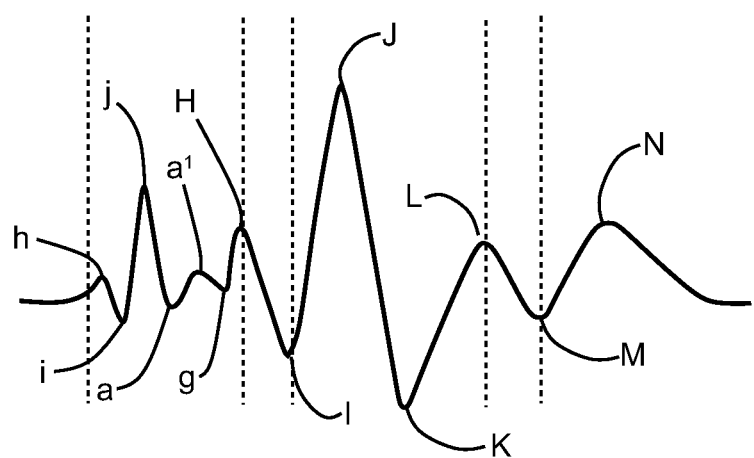

Especially, the signal S1 can be the OA-peak shown in FIG. 3c and the signal S2 can be the J-peak shown in FIG. 1b.

Each peak value, e.g. the height of a single AO-peak shown in FIG. 3c, can be taken as a single point by searching a local maximum. Alternatively, the peak value can be obtained so that many samples are taken first from a time-window covering the peak under consideration and then the peak value is computed as a mathematical function, e.g. an arithmetic mean, of the samples in order to mitigate the effect of noise. The time window can be e.g. 100 ms, and the number of samples within the time window can be e.g. ten or more. The method based on the time-window is an example of digital filtering. Generally, there are numerous digital and analogue signal processing methods that can be used for mitigating the effect of noise in the signals indicative of cardiovascular motion.

It is to be noted that there are numerous ways to express the strength of the amplitude variation and the present invention is not limited to any particular ways of expressing the strength of the amplitude variation.

In a method according to another exemplifying embodiment of the invention:
- the detection of the amplitude variation, i.e. the phase 201 shown in FIG. 2a, comprises detecting maximum signal values of the AO-peaks, and
- the determining of the indicator of cardiac malfunction and abnormality, i.e. the phase 202, comprises computing an amplitude variation quantity indicative of the strength of the variation of the detected maximum signal values.

Figure 4:
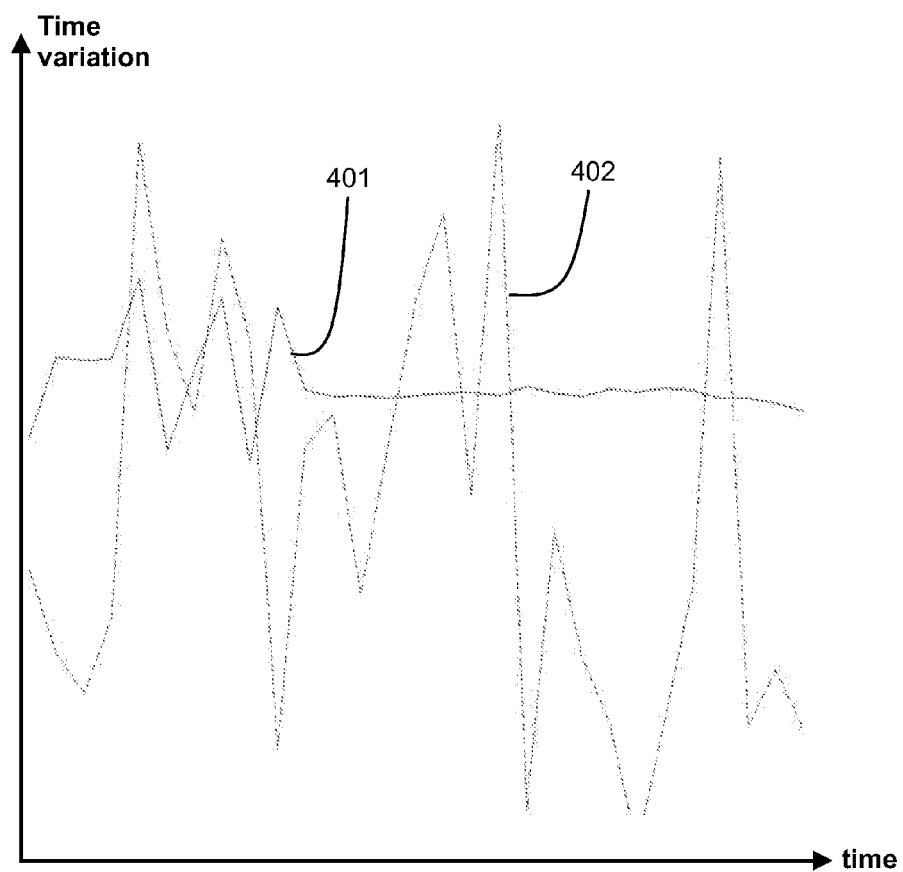
FIG. 4 illustrates an exemplifying time variation in a normal case, solid line, and an exemplifying time variation in a case of atrial fibrillation, dashed line.

A solid curve 401 in FIG. 4 illustrates variation of temporal lengths of successive heart-beat periods, i.e. the time variation, in an exemplifying normal case. The temporal length of a single heart-beat period is denoted with "HB" in FIG. 3b. A dashed curve 402 in FIG. 4 illustrates the time variation in an exemplifying case of atrial fibrillation. As illustrated by FIG. 4, also the strength of the time variation represents information indicative of cardiac malfunction and abnormality.

A method according to an exemplifying embodiment of the invention comprises, in addition to utilizing the amplitude variation, detecting the time variation from the signal indicative of cardiovascular motion. The indicator of cardiac malfunction and abnormality is advantageously determined on the basis of both the amplitude variation and the time variation in order to improve the reliability of the information indicative of cardiac malfunctions and abnormalities.

In a method according to an exemplifying embodiment of the invention, the detection of the time variation comprises detecting temporal lengths of time intervals between successive AO-peaks, and computing a time variation quantity that is indicative of the strength of the variation of the detected temporal lengths.

The indicator of cardiac malfunction and abnormality can be formed, for example, with the aid of a mathematical or logical operation from the amplitude variation quantity indicative of the strength of the amplitude variation and the time variation quantity indicative of the strength of the time variation. It is also possible that the amplitude variation quantity and the time variation quantity are used separately; e.g. each of them is compared to its own threshold.

A method according to an exemplifying embodiment of the invention comprises producing a signal expressing that atrial fibrillation is taking place in response to a situation in which at least one of the following takes place: the strength of the amplitude variation exceeds a first threshold, the strength of the time variation exceeds a second threshold. In this exemplifying embodiment, the risk that atrial fibrillation remains undetected is reduced by indicating the occurrence of the atrial fibrillation if at least one of the amplitude variation and the time variation indicates the occurrence.

A method according to another exemplifying embodiment of the invention comprises producing a signal expressing that atrial fibrillation is taking place if and only if the strength of the amplitude variation exceeds a first threshold and the strength of the time variation exceeds a second threshold. In this exemplifying embodiment, the risk of false alarms is reduced by indicating the occurrence of the atrial fibrillation if and only if both the amplitude variation and the time variation indicate the occurrence.

Figure 2B:
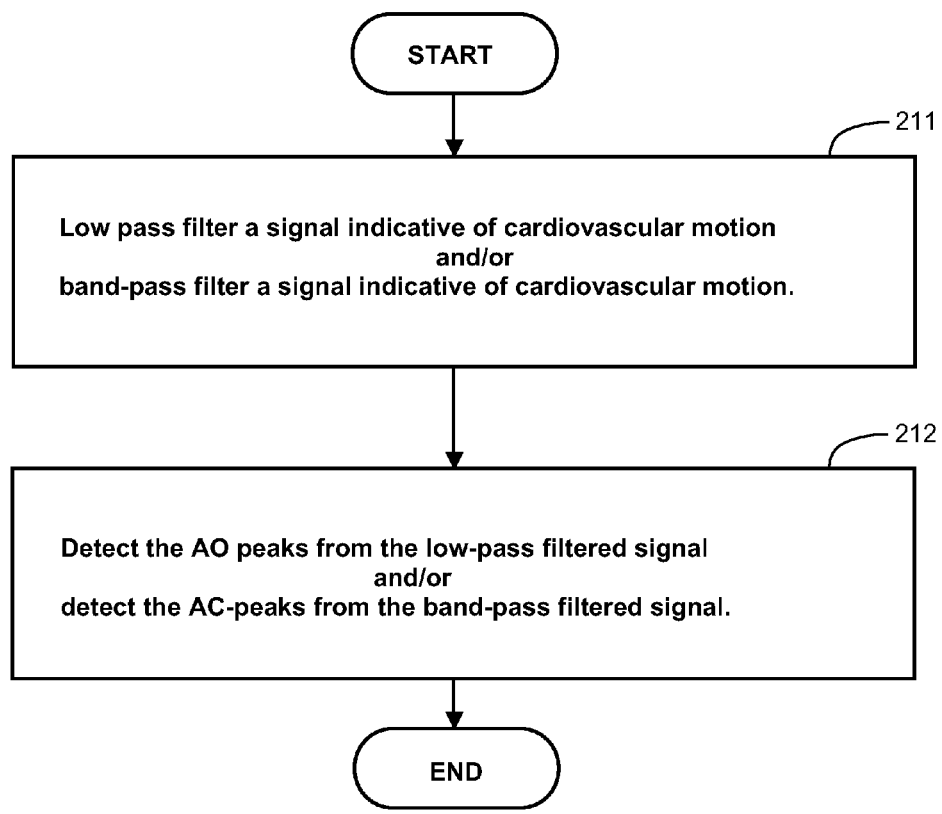
FIG. 2b illustrates a flow chart of a method according to an exemplifying embodiment of the invention for extracting AO data and/or AC data from a signal indicative of the cardiovascular motion.

FIG. 2b illustrates a flow chart of a method according to an exemplifying embodiment of the invention for extracting AO data and/or AC data from a signal indicative of the cardiovascular motion. The signal indicative of the cardiovascular motion is advantageously measured with an accelerometer in the "through chest"-direction that is typically referred to as the z-direction. The method comprises the following actions:
- action 211: low-pass filtering the signal indicative of the cardiovascular motion and/or band-pass filtering the signal indicative of the cardiovascular motion, and
- action 212: detecting the AO-peaks from the low-pass filtered signal and/or detecting the AC-peaks from the band-pass filtered signal.

The upper limit frequency of the low-pass filtering can be, for example but not necessarily, 30 Hz, and the pass-band of the band-pass filtering can be, for example but not necessarily, from 40 Hz up to 100 Hz. The low-pass filtering and/or the pass-band filtering facilitate the detection of the AO- and/or AC-peaks. The detected AO- and/or AC-peaks can be utilized when detecting for example the above-mentioned amplitude variation and/or the above-mentioned time variation. The detected AO- and/or AC-peaks can be used for many other purposes too, e.g. for detecting the heart-beat rate, the systolic intervals, and/or the diastolic intervals.

A method according to an exemplifying embodiment of the invention comprises detecting temporal lengths of AC-AO intervals and computing a time variation quantity indicative of strength of variation of the detected temporal lengths of the AC-AO intervals, where each of the AC-AO intervals is a time interval from one of the AC-peaks to the following one of the AO-peaks and the time variation quantity is indicative of cardiac malfunction and abnormality.

A method according to an exemplifying embodiment of the invention comprises detecting temporal lengths of AC-AO intervals and temporal lengths of AO-AO intervals and computing a ratio quantity indicative of the ratio between the temporal length of the AC-AO interval and the temporal length of the AO-AO interval within a same heart-beat period. Each of the AC-AO intervals is a time interval from one of the AC-peaks to the following one of the AO-peaks, each of the AO-AO intervals is a time interval from one of the AO-peaks to the following one of the AO-peaks, and the ratio quantity is indicative of cardiac malfunction and abnormality.

A method according to an exemplifying embodiment of the invention comprises optionally measuring the signal indicative of cardiovascular motion with a sensor element from an individual's body. A method according to another exemplifying embodiment of the invention comprises reading this signal from a memory, in which case the signal has been measured earlier and recorded to the memory. A method according to an exemplifying embodiment of the invention comprises receiving the signal from an external data transfer system. Hence, the measuring is not an essential and necessary step of methods according to embodiments of the invention.

FIG. 5 illustrates a schematic illustration of an apparatus according to an exemplifying embodiment of the invention for determining information indicative of cardiac malfunctions and abnormalities. The apparatus comprises a signal interface 501 for receiving a signal indicative of cardiovascular motion, and a processing device 502 coupled to the signal interface. The processing device is configured to:

detect amplitude variation from the signal, the amplitude variation being variation of amplitude of a wave pattern repeating on the heart-beat rate on the signal, and
 determine, at least partly on the basis of the amplitude variation, an indicator of cardiac malfunction and abnormality.

The indicator can be, for example, a message shown on a display screen 506.

In an apparatus according to an exemplifying embodiment of the invention, the signal interface 501 is further configured to receive information indicative of frequency of a respiratory rhythm and the processing device 502 is configured to:

compute a signal component of the amplitude variation having the frequency of the respiratory rhythm, and
 determine the indicator of cardiac malfunction and abnormality at least partly on the basis of the signal component of the amplitude variation having the frequency of the respiratory rhythm.

In an apparatus according to an exemplifying embodiment of the invention, the processing device 502 is configured to produce a signal expressing atrial fibrillation in response to a situation in which the signal component of the amplitude variation having the frequency of the respiratory rhythm is less than a pre-determined threshold.

An apparatus according to an exemplifying embodiment of the invention further comprises a sensor element 503 for measuring the signal indicative of cardiovascular motion from individual's body 510. The sensor element is connected to the signal interface via a data transfer link that can be, for example, a radio link or a corded link. The data transfer from the sensor element 503 to the signal interface 501 may take place either directly or via a data transfer network 505 such as e.g. a telecommunications network. It is also possible that the apparatus comprising the processing device is integrated with the sensor element. In this case, the signal interface is actually a simple wiring between the sensor element 503 and the processing device 502. In an apparatus according to an exemplifying embodiment of the invention, the sensor element 503 is also suitable for providing the information indicative of the frequency of the respiratory rhythm.

The sensor element 503 may comprise, for example, an accelerometer, a piezo-electronic sensor, an inclinometer, a pressure sensor, or any other element suitable for measuring force, acceleration, displacement, or any other physical quantity related to and indicative of cardiovascular motion. The sensor element may further comprise, for example, an amplifier, a signal filter, and/or an analog-to-digital "AD" converter. An accelerometer can be, for example, a three-axis accelerometer which is capable of measuring movements independently in three mutually orthogonal directions x, y, and z of e.g. the coordinate system 550 shown in FIG. 5. In this case, the signal indicative of cardiovascular motion comprises three components and the signal can be, for example, pre-processed by forming its Euclidian norm, i.e. the absolute value of the three component vector indicative of cardiovascular motion.

An apparatus according to an exemplifying embodiment of the invention is configured to record the signal within a time window having a fixed temporal start point and a fixed temporal end point or within a sliding time window having a fixed temporal length and moving along with elapsing time. The apparatus may comprise an internal memory 507 for recording the signal or the apparatus may comprise a data port for connecting to an external memory.

In an apparatus according to an exemplifying embodiment of the invention, the processing device 502 is configured to detect peak-to-peak values related to wave complexes each of which being constituted by the AO-peak caused by opening of the aortic valve and the downward wave following the AO-peak, and to compute an amplitude variation quantity indicative of the strength of the variation of the detected peak-to-peak values.

In an apparatus according to an exemplifying embodiment of the invention, the processing device 502 is configured to detect maximum signal values of the AO-peaks, and to compute an amplitude variation quantity indicative of the strength of the variation of the detected maximum signal values.

In an apparatus according to an exemplifying embodiment of the invention, the processing device 502 is configured to detect time variation from the signal and to determine the indicator of cardiac malfunction and abnormality on the basis of both the amplitude variation and the time variation.

In an apparatus according to an exemplifying embodiment of the invention, the processing device 502 is configured to detect temporal lengths of time intervals between successive AO-peaks, and to compute a time variation quantity indicative of the strength of the variation of the detected temporal lengths.

In an apparatus according to an exemplifying embodiment of the invention, the processing device 502 is configured to produce a signal expressing atrial fibrillation in response to a situation in which at least one of the following takes place: the strength of the amplitude variation exceeds a first threshold, the strength of the time variation exceeds a second threshold, the signal component of the amplitude variation having the frequency of the respiratory rhythm is less than a third threshold.

In an apparatus according to an exemplifying embodiment of the invention, the processing device 502 is configured to low-pass filter the signal indicative of the cardiovascular motion and to detect the above-mentioned AO-peaks from the low-pass filtered signal. A functional block 520 shown in FIG. 5 represents of the low-pass filtering, and a functional block 522 represents the detection of the AO-peaks.

In an apparatus according to an exemplifying embodiment of the invention, the processing device 502 is configured to band-pass filter the signal indicative of the cardiovascular motion and to detect AC-peaks from the band-pass filtered signal, the AC-peaks being caused by the closures of the aortic valve. A functional block 521 shown in FIG. 5 represents of the band-pass filtering, and the functional block 522 represents the detecting the AC-peaks. In the exemplifying case illustrated in FIG. 5, there are both the low-pass filtering and the band-pass filtering and the functional block 522 represents the detection of both the AO- and AC-peaks. The upper limit frequency of the low-pass filtering can be, for example but not necessarily, 30 Hz, and the pass-band of the band-pass filtering can be, for example but not necessarily, from 40 Hz up to 100 Hz. The low-pass filtering and/or the pass-band filtering facilitate the detection of the AO- and/or AC-peaks. The detected AO- and/or AC-peaks can be utilized when detecting for example the above-mentioned amplitude variation and/or the above-mentioned time variation. The detected AO- and/or AC-peaks can be used for many other purposes too, e.g. for detecting the heart-beat rate, the systolic intervals, and/or the diastolic intervals.

In an apparatus according to an exemplifying embodiment of the invention, the processing device 502 is configured to detect temporal lengths of AC-AO intervals and to compute a time variation quantity indicative of strength of variation of the detected temporal lengths of the AC-AO intervals. Each of the AC-AO intervals is a time interval from one of the AC-peaks to the following one of the AO-peaks and the time variation quantity is indicative of cardiac malfunction and abnormality.

In an apparatus according to an exemplifying embodiment of the invention, the processing device 502 is configured to detect temporal lengths of AC-AO intervals and temporal lengths of AO-AO intervals and to compute a ratio quantity indicative of the ratio between the temporal length of the AC-AO interval and the temporal length of the AO-AO interval within a same heart-beat period. Each of the AC-AO intervals is a time interval from one of the AC-peaks to the following one of the AO-peaks, each of the AO-AO intervals is a time interval from one of the AO-peaks to the following one of the AO-peaks, and the ratio quantity is indicative of cardiac malfunction and abnormality.

The processing device 502 can be, for example, implemented with one or more processor circuits, each of which can be a programmable processor circuit provided with appropriate software, a dedicated hardware processor such as, for example, an application specific integrated circuit "ASIC", or a configurable hardware processor such as, for example, a field programmable gate array "FPGA".

An apparatus according to an exemplifying embodiment of the invention comprises means for pre-processing the signal indicative of cardiovascular motion prior to the detection of the amplitude variation. The pre-processing may comprise, for example, cancellation of noise caused by e.g. breathing, non-cardiovascular movements of the individual, tremble caused by external reasons, etc. The means for the pre-processing can be, for example, implemented with the processing device 502 or there can be one or more separate processing devices for the pre-processing.

A computer program according to an exemplifying embodiment of the invention comprises software modules for determining information indicative of cardiac malfunctions and abnormalities. The software modules comprise computer executable instructions for controlling a programmable processor to:

detect amplitude variation from a signal indicative of cardiovascular motion, the amplitude variation being variation of amplitude of a wave pattern repeating on the heart-beat rate on the signal, and determine, at least partly on the basis of the amplitude variation, an indicator of cardiac malfunction and abnormality.

In a computer program according to an exemplifying embodiment of the invention, the software modules further comprise computer executable instructions for controlling the programmable processor to:

compute a signal component of the amplitude variation having a frequency of a respiratory rhythm, and determine the indicator of cardiac malfunction and abnormality at least partly on the basis of the signal component of the amplitude variation having the frequency of the respiratory rhythm.

The software modules can be e.g. subroutines or functions implemented with a suitable programming language and with a compiler suitable for the programming language and the programmable processor.

In a computer program according to an exemplifying embodiment of the invention, the software modules comprise at least one of the following:

computer executable instructions for controlling a programmable processor to low-pass filter a signal indicative of the cardiovascular motion and to detect the AO-peaks from the low-pass filtered signal, and/or computer executable instructions for controlling a programmable processor to band-pass filter the signal indicative of the cardiovascular motion and to detect the AC-peaks from the band-pass filtered signal.

A computer program product according to an exemplifying embodiment of the invention comprises a computer readable medium, e.g. a compact disc ("CD"), encoded with a computer program according to an embodiment of invention.

A signal according to an exemplifying embodiment of the invention is encoded to carry information defining a computer program according to an embodiment of invention.

Certain exemplifying new technologies for determining information indicative of cardiac malfunctions and abnormalities are based on the autocorrelation and/or the frequency spectrum of a signal indicative of cardiovascular motion.

The autocorrelation, as a general concept, has the property that, when irregularity of the waveform of a signal under consideration increases, the autocorrelation gets more and more concentrated to a point that corresponds to zero time-shift between signal samples whose mutual correlation is expressed by the autocorrelation. The autocorrelation $R_e$ of an example signal $S_e(t)$ can be defined, for example, as:

$$R_e(\tau) = E\{(S_e(t)-\mu) \times (S_e(t-\tau)-\mu)\}/\sigma^2,$$

where E is the expected value operator, i.e. E{signal} is the expected value of the signal, t is time, $\tau$ is a time-shift between signal samples whose mutual correlation is expressed by $R_e(\tau)$, and $\mu$ and $\sigma^2$ are the mean and the variance of the example signal $S_e(t)$. For example, if the example signal $S_e(t)$ were ideal white noise "IWN" which has extremely irregular waveform, there would be zero correlation between any signal samples separated by a non-zero time-shift, and thus the autocorrelation $R_e(\tau)$ of the example signal would be only a single peak at the point $\tau=0$.

Such cardiac malfunctions and abnormalities, e.g. atrial fibrillation, which may be sometimes challenging to diagnose, may however cause irregularities on the waveform of the signal indicative of cardiovascular motion. These irregularities may be difficult to detect from waveforms of one or two heart-beat periods but they manifest themselves in longer time periods covering several successive heart-beat periods so that the autocorrelation is more concentrated on the point that corresponds to zero time-shift than normally. Therefore, a quantity that indicates the degree of concentration of the autocorrelation to the point that corresponds to the zero time-shift represents information indicative of cardiac malfunctions and abnormalities, e.g. atrial fibrillation.

The obtaining the quantity indicating the degree of concentration of the autocorrelation can be based on computing an estimate of the autocorrelation or on computing an estimate of the frequency spectrum of the signal. The frequency spectrum is closely related to the autocorrelation because the power spectral density "PSD"~F(f)×F*(f) is the Fourier transformation of the autocorrelation, where F(f) and F*(f) are the frequency spectrum and its complex conjugate. The frequency spectrum, as a general concept, has the property that, when irregularity of the waveform of a signal under consideration increases, the frequency spectrum gets more and more evenly distributed. For example, if an example signal were ideal white noise "IWN" which has extremely irregular waveform, the frequency spectrum of the example signal would be totally flat. This property of the frequency spectrum can be used for obtaining the quantity indicating the degree of concentration of the autocorrelation.

Certain exemplifying new apparatuses for determining information indicative of cardiac malfunctions and abnormalities are described below with the aid of numbered Clauses 1-6:

Clause 1. An apparatus comprising:
a signal interface for receiving a signal indicative of cardiovascular motion, and
a processing device coupled to the signal interface and configured to:
a) form an estimate of at least one of the following: the autocorrelation of the signal, the frequency spectrum of the signal, and
b) form an indicator quantity that indicates the degree of concentration of the autocorrelation of the signal to a point that corresponds to zero time-shift between signal samples whose mutual correlation is expressed by the autocorrelation, the indicator quantity being indicative of cardiac malfunction and abnormality.

Clause 2. An apparatus according to Clause 1, wherein the apparatus further comprises a sensor element for measuring the signal, the sensor element being connected to the signal interface via a data transfer link.

Clause 3. An apparatus according to Clause 2, wherein the sensor element comprises one of the following: an accelerometer, a piezo-electronic sensor, an inclinometer, a microphone, a pressure sensor.

Clause 4. An apparatus according to any of Clauses 1-3, wherein the processing device is configured to produce an indicator of atrial fibrillation in response to a situation in which the ratio $P_{max}/B_R$ is at least 1.3, where $P_{max}$ is a value of the highest peak of the estimate of the autocorrelation and $B_R$ is an average of values of one or more next highest peaks of the estimate of the autocorrelation, the ratio $P_{max}/B_R$ representing the indicator quantity.

Clause 5. An apparatus according to any of Clauses 1-3, wherein the processing device is configured to produce an indicator of atrial fibrillation in response to a situation in which the ratio $P_{max}/B_R$ is at least 1.4, where $P_{max}$ is a value of the highest peak of the estimate of the autocorrelation and $B_R$ is an average of values of one or more next highest peaks of the estimate of the autocorrelation, the ratio $P_{max}/B_R$ representing the indicator quantity.

Clause 6. An apparatus according to any of Clauses 1-3, wherein the processing device is configured to produce an indicator of atrial fibrillation in response to a situation in which the ratio $P_{max}/B_R$ is at least 1.4, where $P_{max}$ is a value of the highest peak of the estimate of the autocorrelation and $B_R$ is an average of values of one or more next highest peaks of the estimate of the autocorrelation, the ratio $P_{max}/B_R$ representing the indicator quantity.

Certain exemplifying new methods for determining information indicative of cardiac malfunctions and abnormalities are described below with the aid of numbered Clauses 7-10:

Clause 7. A method comprising:
forming an estimate of at least one of the following: the autocorrelation of a signal indicative of cardiovascular motion, the frequency spectrum of the signal, and
forming an indicator quantity that indicates the degree of concentration of the autocorrelation of the signal to a point that corresponds to zero time-shift between signal samples whose mutual correlation is expressed by the autocorrelation, the indicator quantity being indicative of cardiac malfunction and abnormality.

Clause 8. A method according to Clause 7, wherein the method comprises producing an indicator of atrial fibrillation in response to a situation in which the ratio $P_{max}/B_R$ is at least 1.3, where $P_{max}$ is a value of the highest peak of the estimate of the autocorrelation and $B_R$ is an average of values of one or more next highest peaks of the estimate of the autocorrelation, the ratio $P_{max}/B_R$ representing the indicator quantity.

Clause 9. A method according to Clause 7, wherein the method comprises producing an indicator of atrial fibrillation in response to a situation in which the ratio $P_{max}/B_R$ is at least 1.4, where $P_{max}$ is a value of the highest peak of the estimate of the autocorrelation and $B_R$ is an average of values of one or more next highest peaks of the estimate of the autocorrelation, the ratio $P_{max}/B_R$ representing the indicator quantity.

Clause 10. A method according to Clause 7, wherein the method comprises producing an indicator of atrial fibrillation in response to a situation in which the ratio $P_{max}/B_R$ is at least 1.4, where $P_{max}$ is a value of the highest peak of the estimate of the autocorrelation and $B_R$ is an average of values of one or more next highest peaks of the estimate of the autocorrelation, the ratio $P_{max}/B_R$ representing the indicator quantity.

A new computer program for determining information indicative of cardiac malfunctions and abnormalities is described below with the aid of a numbered Clause 11.

Clause 11. A computer program comprising computer executable instructions for controlling a programmable processor to:
form an estimate of at least one of the following: the autocorrelation of a signal indicative of cardiovascular motion, the frequency spectrum of the signal, and
form an indicator quantity that indicates the degree of concentration of the autocorrelation of the signal to a point that corresponds to zero time-shift between signal samples whose mutual correlation is expressed by the autocorrelation, the indicator quantity being indicative of cardiac malfunction and abnormality.

A new computer program product for determining information indicative of cardiac malfunctions and abnormalities is described below with the aid of a numbered Clause 12.

Clause 12. A computer program product comprising a non-transitory computer readable medium encoded with a computer program according to Clause 11.

The specific examples provided in the description given above should not be construed as limiting the scope and/or the applicability of the appended claims. Furthermore, it is also to be noted that, in many cases, the present invention can be used together with other techniques for detecting cardiac malfunctions and abnormalities.

What is claimed is:

1. An apparatus, comprising:
   a signal interface, that receives a signal indicative of cardiovascular motion, and that receives information indicative of a frequency of a respiratory rhythm; and
   a processing device coupled to the signal interface,
   wherein the processing device is configured to:
      detect peak-to-peak amplitude variation from the signal, the peak-to-peak amplitude variation being a variation of peak-to-peak amplitude of a wave pattern repeating on a heart-beat rate on the signal so that the peak-to-peak amplitude variation includes a plurality of increases of the peak-to-peak amplitude and a plurality of decreases of the peak-to-peak amplitude,
      compute a signal component of the peak-to-peak amplitude variation having the frequency of the respiratory rhythm, and
      produce a signal expressing atrial fibrillation in response to a situation in which the signal component of the peak-to-peak amplitude variation having the frequency of the respiratory rhythm is less than a threshold, and
   wherein, in detecting the peak-to-peak amplitude variations from the signal, the processing device operates to filter the signal, and the peak-to-peak amplitude variation is determined from peaks detected from the filtered signal.

2. The apparatus according to claim 1, wherein the apparatus further comprises:
   a sensor element that measures said signal, the sensor element being connectable to the signal interface.

3. The apparatus according to claim 2, wherein the sensor element provides to the signal interface the information indicative of the frequency of the respiratory rhythm.

4. The apparatus according to claim 2, wherein the sensor element comprises one selected from the group consisting of: an accelerometer, a piezo-electronic sensor, an inclinometer, and a pressure sensor.

5. The apparatus according to claim 1, wherein the processing device is configured to detect from the signal peak-to-peak values related to wave complexes, each of which being constituted by the AO-peak caused by opening of the aortic valve and the downward wave following the AO-peak, the wave pattern repeating on the heart-beat rate being constituted by the AO-peak and the downward wave following the AO-peak.

6. The apparatus according to claim 5, wherein the processing device is configured to low-pass filter the signal indicative of the cardiovascular motion and to detect the AO-peaks from the low-pass filtered signal.

7. The apparatus according to claim 6, wherein an upper limit frequency of the low-pass filtering is 30 Hz.

8. The apparatus according to claim 5, wherein the processing device is configured to band-pass filter the signal indicative of the cardiovascular motion and to detect AC-peaks from the band-pass filtered signal, the AC-peaks being caused by closures of the aortic valve.

9. The apparatus according to claim 8, wherein a pass-band of the band-pass filtering is from 40 Hz to 100 Hz.

10. A method, comprising:
    receiving a signal indicative of cardiovascular motion;
    applying a filter to said signal so as to generate a filtered signal indicative of said cardiovascular motion;
    detecting peak-to-peak amplitude variation from the filtered signal indicative of cardiovascular motion, the peak-to-peak amplitude variation being a variation of peak-to-peak amplitude of a wave pattern repeating on a heart-beat rate on the filtered signal, such that the peak-to-peak amplitude variation includes a plurality of increases of the peak-to-peak amplitude and a plurality of decreases of the peak-to-peak amplitude;
    computing a signal component of the peak-to-peak amplitude variation having a frequency of a respiratory rhythm; and
    producing a signal expressing atrial fibrillation in response to a situation in which the signal component of the peak-to-peak amplitude variation having the frequency of the respiratory rhythm is determined to be lower than a threshold.

11. The method according to claim 10, wherein the detecting of the peak-to-peak amplitude variation comprises detecting peak-to-peak values related to wave complexes, each of which being constituted by the AO-peak caused by opening of the aortic valve and the downward wave following the AO-peak.

12. The method according to claim 11, wherein the filter applies low-pass filtering to the signal indicative of the cardiovascular motion, and the detecting step detects the AO-peaks from the low-pass filtered signal.

13. The method according to claim 12, wherein an upper limit frequency of the low-pass filtering is 30 Hz.

14. The method according to claim 11, wherein the filter applies band-pass filtering to the signal indicative of the cardiovascular motion, and the detecting step detects AC-peaks from the band-pass filtered signal, the AC-peaks being caused by closures of the aortic valve.

15. The method according to claim 14, wherein a pass-band of the band-pass filtering is from 40 Hz to 100 Hz.

16. A non-transitory computer readable medium encoded with a computer program comprising computer executable instructions for controlling a programmable processor, the computer executable instructions configured such to, upon execution by the programmable processor, cause the programmable processor to:
    receive a signal indicative of cardiovascular motion;
    apply a filter to said signal so as to generate a filtered signal indicative of said cardiovascular motion;
    detect peak-to-peak amplitude variation from the filtered signal indicative of cardiovascular motion, the peak-to-peak amplitude variation being variation of peak-to-peak amplitude of a wave pattern repeating on a heart-beat rate on the filtered signal, such that the peak-to-peak amplitude variation includes a plurality of increases of the peak-to-peak amplitude and a plurality of decreases of the peak-to-peak amplitude;
    compute a signal component of the amplitude variation having a frequency of a respiratory rhythm;

determine whether the signal component of the peak-to-peak amplitude variation having the frequency of the respiratory rhythm is lower than a threshold; and in the event the signal component of the peak-to-peak amplitude variation having the frequency of the respiratory rhythm is determined to be lower than the threshold, produce a signal expressing atrial fibrillation.

* * * * *